United States Patent [19]

Knifton et al.

[11] Patent Number: 5,430,198
[45] Date of Patent: Jul. 4, 1995

[54] DIISOPROPYL EHTER/MTBE COGENERATION FROM CRUDE BY-PRODUCT ACETONE

[75] Inventors: John F. Knifton, Austin; Pei-Shing E. Dai, Port Arthur, both of Tex.

[73] Assignee: Texaco Chemical Inc., White Plains, N.Y.

[21] Appl. No.: 148,244

[22] Filed: Nov. 8, 1993

[51] Int. Cl.$^6$ .................... C07C 41/00; C07C 29/14
[52] U.S. Cl. ................... 568/698; 568/881
[58] Field of Search ................ 568/698, 881

[56] References Cited

U.S. PATENT DOCUMENTS

| | | |
|---|---|---|
| 2,845,461 | 7/1958 | Winkler et al. . |
| 3,351,635 | 11/1967 | Kollar . |
| 3,478,108 | 11/1969 | Grane . |
| 4,036,905 | 7/1977 | Kornfeld . |
| 4,408,081 | 10/1983 | Foster . |
| 4,827,048 | 4/1989 | Knifton . |
| 4,886,918 | 12/1989 | Sorensen et al. ............ 568/698 |
| 4,918,244 | 4/1990 | Nelson et al. . |
| 4,925,989 | 5/1990 | Hagan et al. . |
| 5,081,318 | 1/1992 | Knifton . |
| 5,081,321 | 1/1992 | Fukukara et al. ............ 568/881 |
| 5,102,428 | 4/1992 | Owen et al. ............ 568/698 |
| 5,146,034 | 9/1992 | Morales et al. . |
| 5,157,161 | 10/1992 | Knifton . |
| 5,162,592 | 11/1992 | Knifton et al. ............ 568/698 |
| 5,179,052 | 1/1993 | Knifton . |
| 5,183,947 | 2/1993 | Knifton et al. . |
| 5,214,217 | 5/1993 | Knifton . |
| 5,214,218 | 5/1993 | Knifton . |
| 5,220,078 | 6/1993 | Knifton et al. . |
| 5,276,212 | 1/1994 | Luebke et al. . |

*Primary Examiner*—Johann Richter
*Assistant Examiner*—Rebecca Cook
*Attorney, Agent, or Firm*—James L. Bailey; Kenneth R. Priem; Cynthia L. Hunter

[57] ABSTRACT

Disclosed is a two-step process for the generation of diisopropyl ether from a crude by-product acetone stream which comprises:

a) Hydrogenating said crude acetone over a bulk-metal, nickel-rich catalyst to give an isopropanol-rich effluent;

b) Dehydrating said isopropanol-rich intermediate in the presence of a strong acid zeolite catalyst from the group consisting of $\beta$-zeolite, optionally modified with one or more metals from Group IB, VB, VIB, VIIB and VIII of the Periodic Table, and a dealuminized Y-zeolite, wherein the dehydration temperature is from about 80° C. to 200° C.

19 Claims, No Drawings

DIISOPROPYL EHTER/MTBE COGENERATION FROM CRUDE BY-PRODUCT ACETONE

CROSS-REFERENCE

This application is related to U.S. Ser. Nos. 08/096,873; 08/057,373; and allowed U.S. application Ser. No. 08/148,248. It is also related to U.S. Pat. Nos. 4,822,921; 4,827,048; 5,099,072; 5,081,318; 5,059,725; 5,157,162; 5,162,592; 5,157,161; 5,183,947; and allowed U.S. Ser. Nos. 07/917,218; 07/878,121; and 07/917,885, all of which are incorporated by reference herein in their entirety.

FIELD OF THE INVENTION

This invention concerns a novel two-step procedure for cogeneration of diisopropyl ether (DIPE), and optionally methyl t-butyl ether (MTBE), from a crude by-product acetone stream which comprises (1) hydrogenating the crude acetone stream over a bulk-metal nickel-rich catalyst to give an isopropanol-rich effluent; and (2) subjecting the isopropanol-rich intermediate to dehydrogenation conditions in the presence of a series of strong acid zeolite catalysts from the group consisting of a β-zeolite, dealuminized Y-zeolite and metal-modified β-zeolites to yield a mix of DIPE and MTBE.

DIPE may be used in addition to MTBE as an octane enhancer in gasoline.

BACKGROUND OF THE INVENTION

It is known to those skilled in the art that ethers, including both symmetrical and unsymmetrical ethers, may be prepared by reacting an alcohol with another alcohol to form the desired product. The reaction mixture, containing catalyst and/or condensing agent may be separated and further treated to permit attainment of the desired product. Such further treatment commonly includes one or more distillation operations.

Methyl tert-butyl ether is finding increasing use as a blending component in high octane gasoline as the current gasoline additives based on lead and manganese are phased out. Currently all commercial processes for the manufacture of methyl tert-butyl ether are based upon the liquid-phase reaction of isobutylene and methanol (Eq. 1), catalyzed by a cationic ion-exchange resin (see, for example: *Hydrocarbon Processing*, Oct. 1984, p. 63; Oil and Gas J., Jan. 1, 1979, p. 76; *Chem. Economics Handbook-SRI*, Sept. 1986, p. 543-7051P). The cationic ion-exchange resins used in MTBE synthesis normally have the sulphonic acid functionality (see: J. Tejero, *J. Mol. Catal.*, 42 (1987) 257; C. Subramamam et al., *Can. J. Chem. Eng.*, 65 (1987) 613).

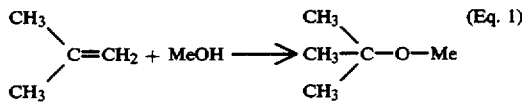

(Eq. 1)

With the expanding use of MTBE as an acceptable gasoline additive, a growing problem is the availability of raw materials. Historically, the critical raw material is isobutylene (Oil and Gas J., Jun. 8, 1987, p. 55). It would be advantageous, therefore, to have a process to make MTBE that does not require isobutylene as a building block.

The use of zeolites for certain reactions is known in the art, β-zeolite was first synthesized at Mobil R&D labs and exhibited improved thermal and acid stability over previously synthesized zeolites.

One of the earliest disclosures of zeolite beta was in U.S. Pat. No. 3,308,069 (1967) to Wadinger et al.

J. B. Higgins, et al. of Mobil Research and Development published an article in *Zeolites*, 1988, Vol. 8, November, 446–452 titled "The Framework Topology of Zeolite Beta." In the article Higgins et al. disclose what is known about the framework topology of zeolite beta. The information has been determined using a combination of model building, distance-least-square refinement and powder pattern simulation.

In an article titled "Cumene Disproportionation over Zeolite β I. Comparison of Catalytic Performances and Reaction Mechanisms of Zeolites," *Applied Catalysis*, 77 (1991) 199–207, Tseng-Chang Tsai, Chin-Lan Ay and Ikai Wang disclose a study demonstrating that cumene disproportionation can be applied as a probe reaction for zeolite structure. It is revealed that zeolite beta would have application potential in the production of diisopropylbenzene for reasons of activity, selectivity and stability.

In a second part of the article, "II. Stability Enhancement with Silica Deposition and Steam Pretreatment", Ibid, pp. 209–222, Tsai and Wang disclose their development of two methods to improve the stability of zeolite beta, silica deposition and steam pretreatment.

Patents in the art which employ zeolite beta relate mainly to dewaxing, and cracking of hydrocarbon feedstock.

An article titled "*Beta Zeolite as Catalyst or Catalyst Additive for the Production of Olefins During Cracking or Gas Oil*," was written by L Bonetto et al , 9th International Zeolite Conference, July 1992, FP 22. The authors note that with the greater demand for oxygenated compounds there is indication there might be increased demands for catalysts and conditions which maximize $C_3$, $C_4$ and $C_5$ olefins. They suggest that β-zeolite could be used alone or combined with Y-zeolite as a suitable zeolite component. Various catalysts were studied with respect to minimization of diffusional requirements and zeolite stability.

U.S. Pat. No. 4,419,220, to Mobil, discloses a process for dewaxing a hydrocarbon feedstock containing straight chain paraffins which comprises contacting the feedstock with a β-zeolite beta catalyst having a Si:Al ratio of at least 30:1 and a hydrogenation component under isomerization conditions.

Another European Application to Mobil, EP 0 094 82, discloses simultaneous catalytic hydrocracking and hydrodewaxing of hydrocarbon oils with β-zeolite.

In European Patent Application 0 095 303, to Mobil, there is a disclosure of dewaxing distillate fuel oils by the use of β-zeolite catalysts which, preferably have a silica:alumina ratio over 100:1. Ratios as high as 250:1 and 500:1 are disclosed as useful.

Another U.S. Pat. No. 4,518,485, to Mobil, discloses a process for dewaxing a hydrocarbon feedstock containing paraffins selected from the group of normal paraffins and slightly branched paraffins and sulfur and nitrogen compounds where, after conventionally hydrotreating the feedstock to remove sulfur and nitrogen, the hydrotreated feedstock is dewaxed by contacting the feedstock with a catalyst comprising a β-zeolite having a silica/alumina ratio of at least 30:1.

In U.S. Pat. No. 4,740,292, to Mobil, there is disclosed a catalytic cracking process which comprises cracking a hydrocarbon feed in the absence of added hydrogen with a cracking catalyst comprising a β-zeolite component and a faujasite component comprising at least one crystalline aluminosilicate of the faujasite structure, the weight ratio of the faujasite component to the β-zeolite component being from 1:25 to 20:1.

Large pore β-zeolite has been employed in the synthesis of industrially important para-cumene by toluene isopropylation. See "Toluene Isopropylation over Zeolite β and Metallosilicates of MFI Structure," P. A. Parikh et al., *Applied Catalysis, A*, 1992, 90, p. 1.

Japanese Patent 82-07432 teaches the use of zeolites, particularly mordenites and faujasites, to make dialkyl ethers containing primary or secondary alkyl groups by the liquid phase dehydration of alcohols.

U. S. Pat. No. 4,058,576 to Chang et al. teaches the use of (pentasil-type) aluminosilicate zeolites, such as ZSM-5, having a pore size greater than 5 angstrom units and a silica-to-alumina ratio of at least 12, to convert lower alcohols to a mixture of ethers and olefins.

In allowed U.S. Pat. No. 5,214,217 there is disclosed a method for preparing methyl tertiary butyl ether by reacting butanol and methanol in the presence of a catalyst comprising a super-acid alumina or a faujasite-type zeolite.

In U.S. Pat. No. 5,081,318, a Y-type zeolite modified with fluorosulfonic acid is disclosed.

In U.S. Pat. No. 3,955,939 to Sommer et al. (1976), there is disclosed the production of a water-free mixture of isopropyl alcohol, diisopropyl alcohol, diisopropyl ether and by-products by the catalytic hydration of propylene in the gaseous phase at temperatures of 140°-170° C., wherein the water-free mixture formed according to the process can be used directly as an additive to gasoline fuel.

In European Patent 323138 and U.S. Pat. No. 4,906,787, there is disclosed a catalytic process for converting light olefins to ethers suitable as high octane blending stocks carried out by contacting the olefin, especially propene, with water and alcohol recovered from a downstream distillation operation in an olefin conversion unit in the presence of an acidic zeolite catalyst. In this work diisopropyl ether (DIPE) was prepared from $C_3H_6$ and aqueous iso-PrOH in the presence of silica-bound zeolite Beta catalyst at 166°.

Another European Patent, EP 323268, light olefins are converted to alcohols and/or ethers in the presence of β-zeolite.

In U.S. Pat. No. 5,144,086, to Harandi et al., there is disclosed an integrated multistage process for the production of diisopropyl ether and substantially pure propene wherein in the second stage isopropanol containing about 0-20% water is contacted with an acidic large pore zeolite etherification catalyst which comprises a β-zeolite having a Si:Alumina ratio of about 30:1 to 50:1.

In U.S. Pat. No. 5,208,387, also to Harandi et al., there is disclosed a process for the acid catalyzed production of DIPE from propene and water feed stream that eliminates the propene recycle stream to the olefin hydration reactor and achieves high propene conversion. This process is carried out in two stages wherein the first stage comprises a zeolite catalyzed hydration and etherification of propene employing a minimum of water feed and the second stage converts unconverted propene from the first stage reactor by hydration and etherification to DIPE.

In an article titled "*Race to License New MTBE and TAME Routes Heats Up*", Rotman, D., *Chemical Week*, Jan. 6, 1993, p. 48, there is a review of new technology at several different companies which centers around skeletal isomerization, particularly of $C_4$ and $C_5$ olefins. The interest in this technology is fueled by the promise of dramatically increased and relatively inexpensive isobutylene and isoamylene that could boost MTBE and TAME production, often constrained by the amounts of available isobutylene in refinery or steam cracker streams. DIPE production from propylene is also discussed.

Mobil Corp. has disclosed new etherification technology that can produce fuel oxygenates based only on olefinic refinery streams and water. This process has the potential to allow refiners to produce oxygenates without having to rely on an external supply of alcohols. The technology is developed around diisopropyl ether (DIPE) based on propylene. The DIPE has similar physical and blending activities to MTBE and TAME and is a perfectly acceptable fuel oxygen source. Wood, A., *Chemical Week*, Apr. 15, 1992, p. 7.

None of the available references would seem to suggest the conversion of the acetone portion present in a by-product stream into useful oxygenates. The portion of said by-product stream which typically comprises acetone is about 20% to 80%. It would greatly enhance the economics of any process to produce MTBE or other oxygenates if acetone from a by-product stream could be converted to useful oxygenate products such as diisopropyl ether (DIPE).

SUMMARY OF THE INVENTION

In accordance with the foregoing the novel method of the instant invention for generation of diisopropyl ether from a crude by-product acetone stream is a two-step process which comprises:

(1) hydrogenating the crude acetone stream over a bulk-metal nickel-rich catalyst to give an isopropanol rich effluent; and (2) Dehydrating the isopropanol-rich intermediate in the presence of a series of strong acid zeolite catalysts from the group consisting of β-zeolite, dealuminized Y-zeolites and metal-modified β-zeolites to yield DIPE.

DETAILED DESCRIPTION OF THE INVENTION

Cogeneration of methyl t-butyl ether and diisopropyl ether may also be accomplished in the instant invention by the steps listed above, where the by-product acetone stream, in addition, contains significant quantities—that is preferably greater than 5%—of both methanol (MeOH) and t-butanol (tBA). Most preferably, for the cogeneration of DIPE and MTBE, the crude acetone feed contains 10%-40% each of both methanol and t-butanol.

The two-step DIPE synthesis can be represented by:

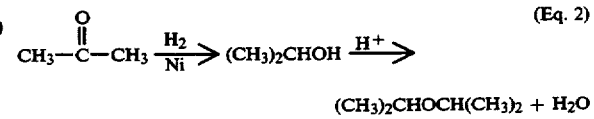

(Eq. 2)

In a process to make propylene oxide a large number of by-products are typically generated with the desired product. The by-products may include formic acid, acetic acid, their ester derivatives, t-butanol and acetone. The acetone may constitute about 20% to 80% of certain crude by-product streams. These crude acetone streams may be further mixed with methanol. The stream preferably contains greater than 5% of both methanol and t-butanol. Most preferably, for the cogeneration of DIPE and MTBE, the crude acetone feed contains 10%–40% each of both methanol and t-butanol. In Example 1 of the instant invention, for example, the crude acetone stream contains 61.7% acetone, 13.9% methanol, 16.7% t-butanol and 0.1% isopropanol.

In the first step the crude acetone is passed over a nickel-rich catalyst. A preferred nickel catalyst is characterized by having the composition, calculated in mol %, of from about 60%–85% nickel, 1%–30% copper and 0.1%–6% chromium with the preferred proportions being about 65%–78% nickel, 10%–20% copper and 1%–3% chromium. The temperature necessary to achieve the desired acetone hydrogenation to isopropanol (IPA) is $>100°$ C., the preferable range is $120°–180°$ C.

The conversion of acetone to isopropanol in the first step (Eq. 2) is normally $>90\%$ per pass in continuous processing and preferably it is as great as 99% or more. In the second step the isopropanol is subjected to dehydration conditions in the presence of a series of strong acid zeolite catalysts, from the group consisting of β-zeolite, optionally further modified with one or more metals, or a dealuminized Y-zeolite.

The composition of zeolite beta is described in U.S. Pat. Nos. 3,308,069; 4,419,220; 4,518,485 and 4,740,292. In those references, zeolite beta is typically described as follows:

Zeolite beta is a crystalline aluminosilicate having a pore size greater than 5 Angstroms. The composition of the zeolite, as described in U.S. Pat. No. 3,308,069, in its as synthesized form may be expressed as follows:

where X is less than 1, preferably less than 0.7; TEA represents the tetraethylammonium ion; Y is greater than 5 but less than 100; and W is up to about 60 (it has been found that the degree of hydration may be higher than originally determined, where W was defined as being up to 4), depending on the degree of hydration and the metal cation present. The TEA component is calculated by differences from the analyzed value of sodium and the theoretical cation to structural aluminum ratio of unity.

As discussed in the J. B. Higgins, et al. reference, Supra, p. 446, the first clues to the crystal structure of zeolite beta were evidenced from chemical and physical property measurements. Ion-exchange isotherms of Na-β at 25° C. indicated that cations as large as tetraethylammonium (TEA+) exchanged completely into the pore system. This behavior suggests that beta contains at least 12-membered rings opening into channels, because TEA+ is too large to exchange through 10-membered rings such as those in ZSM-5. The complete exchange of cations in beta indicated the presence of channels instead of cages, because it is not possible to remove all the cations from cage structures such as Na faujasite. Additional evidence was obtained from organic sorption data and density measurements. Cyclohexane sorption of 14.6–19.4 wt % and a measured density of 1.61 g/cm³ ruled out undimensional pore systems such as those in ZSM-12, ZSM-22, ZSM-23 and ZSM-48. Structural similarities among beta, mordenite and ZSM-12 were suspected because all three may be synthesized in Na+—TEA+ systems from highly siliceous batch compositions. Further, zeolite beta is easily synthesized in the SiO₂/Al₂O₃ range of 30–50. This lies between TEA+ mordenite (typically 10–30) and ZSM-12 (typically, $>60$), suggesting the beta framework contains large fractions of both 4- and 5-membered rings.

In the Tsai and Wang reference, Supra, part II, p. 209, stability enhancement is discussed. Two methods, silica deposition and steam pretreatment, have been developed to substantially improve zeolite beta stability.

Ibid, po 215, it is stated that zeolite beta has two types of three dimensional pore openings, the linear and the tortuous channel. The former has pore openings of 7.5 Å×5.7 Å and the latter has pore openings of 6.5 Å×5.6 Å. When silica, for example, is deposited on zeolite beta, the pore opening was narrowed or blocked by the deposited silica. It was concluded that silica deposition selectively removes strong acid sites and increases the population of medium acid sites.

In the fully base-exchanged form, zeolite beta has the composition:

where X, Y and W have the values listed above and n is the valence of the metal M. This form of the zeolite may be converted partly to the hydrogen form by calcination, e.g. at 200° C. to 900° C. or higher. The completely hydrogen form may be made by ammonium exchange followed by calcination in air or an inert atmosphere such as nitrogen, see U.S. Pat. No. 4,419,220.

Zeolite beta is characterized by the following X-ray diffraction pattern:

d Values of Reflection in zeolite beta
11.40±0.2
7.40±0.2
6.70±0.2
4.25±0.1
3.97±0.1
3.00±0.1
2.20±0.1

The preferred forms of zeolite beta are the highly acidic, high silica forms, having silica-to-alumina mole ratio of at least 10:1, and preferably in the range of 10:1 to 50:1 in the as-synthesized form, and a surface area of at least 100 m²/g.

Suitable β-zeolites for the practice of this invention include Valfor C806β, Valfor CP815β and Valfor C861. Valfor ® is the registered trademark of the PQ Corporation. Valfor ® C806β zeolite is zeolite beta powder in template cation form. It is a high silica shape selective zeolite which contains the organic template used in the crystallization step, having been isolated after filtration and washing of the synthesis product. C806β has a SiO₂/Al₂O₃ molar ratio of 23–26; the crystal size is 0.1–0.7 um; the surface area after calcination is about 700–750 m²/g; the cyclohexane adsorption capacity after calcination is 19–24 g/100 g; Na₂O content is about 0.01–1.0% by weight anhydrous; and, the organic content is about 11–13% by weight, on a water-free basis.

Valfor ® C815β zeolite is a calcined zeolite beta powder in hydrogen, sodium form. It is similar to C806β except the product has been calcined to decompose the organic template. C815β is a high silica, shape selective aluminosilicate with a large pore diameter. C815β also has a $SiO_2/Al_2O_3$ molar ratio of about 23–26; the crystal size, surface area, cyclohexane adsorption capacity and Na2O are all within the same ranges as given for C806β.

Valfor ® C861β is an extrudate made of 80% C815β powder and 20% alumina powder.

Said β-zeolites may optionally be modified with a halogen, a halogen-containing organic compound, or a halogen-containing acid. Said halogen may be fluorine, chlorine, bromine or iodine, but is preferably fluorine. In the case of fluoride treatment, the fluoride content of the treated β-zeolite may be in the range of 0.1 to 10 wt %, but preferably is about 1%. Said fluoride-treated zeolites may optionally be calcined, at temperatures of 200° C. and above, prior to further usage or modification.

Said catalysts may be formed in the presence of a binder, such as Group III or Group IV oxide. Group IV oxides used in conjunction with said β-zeolite include oxides of aluminum, silicon, titanium, zirconium, hafnium, germanium, tin and lead, as well as combinations thereof. Alumina is preferred. Said binders may comprise 10% to 90% of the formed catalyst.

Particularly effective in the subject cogeneration of MTBE and DIPE are the β-zeolites modified with multiple metals.

The metals useful for modifying the zeolite in the instant invention comprise those from Groups IB, VB, VIB, VIIB and VIII of the Periodic Table, including said transition metals. Preferred metals are those found in Groups IB, VIB, VIIB and VIII of the Periodic Table and include copper, chromium, manganese, iron, nickel, palladium and platinum. Especially good results were observed using combinations of iron, manganese and chromium or combinations of nickel and copper on VALFOR ® Zeolite 861β.

Said zeolites are preferably impregnated with said specified metals as their salts, particularly their metal nitrate or chloride salts, in an aqueous, alcoholic, or ketonic media over a period of 1–24 hours, then the solids are filtered off, dried at elevated temperature, e.g. 120° C., for a period of time and calcined at 300°–800° C. for a further period, e.g. 315° C. for 2 hours, followed by 540° C. for another 2 hours, then reduced in a stream of hydrogen at $\geq 200°$ C.

The amount of the various metals deposited on the zeolite can vary. The amount of each individual metal, i.e., iron, chromium, copper, manganese, and nickel, can vary from 0.01 to 10.0%. Where iron, chromium and manganese are deposited on 861β the preferred weight percent is from 0.1% to 5.0%.

The second type of catalyst suitable for the second stage of this invention generally comprise dealuminated Y-zeolite catalysts.

The preferred catalysts for use in the dealuminated form for the reaction of Eq. 2 are certain crystalline aluminosilicate zeolites, particularly the isostructural group of faujasite zeolites that include the synthetic X- and Y-zeolites. The preferred zeolites for dealumination are the Y-zeolites.

The unit cells of faujasite zeolites are cubic, $a_o \approx 2.5$ nm, and each contains 192 silicon- or aluminum-centered oxygen tetrahedra which are linked through shared oxygen atoms. Because of the net negative charge on each of the aluminum-centered tetrahedra, each unit cell contains an equivalent number of charge-balancing cations. These are exclusively sodium ions in zeolites in their synthesized form. Typical cell contents for the Y-zeolites in the hydrated form are:

$$Na_{56}[(AlO_2)_{56}(SiO_2)_{136}]x.250\ H_2O$$

Y-zeolites are distinguished on the basis of the relative concentration of silicon and aluminum atoms and the consequent effects on detailed structure and related chemical and physical properties. The aluminum atoms in the unit cell of Y-zeolite vary from 76 to 48, resulting in a Si:Al ratio between 1.5 and 3.0. Both the cation concentration and charge density on the aluminosilicate structure are lower for Y-zeolites than for X-zeolites, where the aluminum atoms in the unit cell vary from 96 to 77.

The feature which determines the difference between faujasites and other zeolites built up from sodalite units is the double 6-membered ring or hexagonal prism, by which the units are linked. The sodalite unit, or β-cage, can be represented by a truncated octahedron, with the 24 silicon or aluminum atoms(designated T atoms) taking positions at the vertices. The 36 oxygen atoms are displaced from the midpoints of the edges joining the vertices in order to attain tetrahedral configuration around the T atoms. The free diameter of the void within the β-cage is 0.66 nm, but only the smallest molecules can enter through the 0.22 nm diameter opening in the distorted ring of six oxygen atoms associated with each hexagonal face. Each sodalite unit is linked tetrahedrally across hexagonal faces by six bridging oxygens to four other sodalite units. The larger void spaces enclosed by sodalite units and hexagonal prisms are termed α-cages, or supercages. The α-cage is a 26-hedron with a free diameter of $\approx 1.3$ nm, and it can be entered through four distorted 12-member rings of diameter 0.80–0.90 nm. In this way each α-cage is tetrahedrally joined to four others giving a complex system of void space extending throughout the zeolite structure. The α- and β-cages together give Y-zeolites, along with X-zeolites, the largest void volume of any known zeolites, which is ca. 50 vol % of the dehydrated crystal. From the catalytic viewpoint, the α-cages are by far the most important, since, unlike the β-cages, they permit entry of numerous aliphatic and aromatic compounds.

It has been demonstrated in the instant invention these Y-zeolites are particularly effective in the dealuminated form. Preferably, said Y-zeolites are dealuminated by ammonium exchange followed by calcination, or by treatment with ethylenediaminetetraacetic acid (EDTA) or other chelating agents or by treatment with fluorine or a fluorine-containing compound such as silicon tetrafluoride or ammonium fluorosilicate, or hydrothermal treatment and/or acid treatment. Said dealuminated Y-zeolites should have a silica-to-alumina molar ratio of greater than three, preferably a ratio of 5 or greater and most preferably a silica-to-alumina ratio of 5 to 100. The examples demonstrate the usefulness of catalysts having a silica-to-alumina ratio of 5 to 25 and particularly 5 to 10.

Examples of suitable commercially available dealuminized Y-zeolites include UOP's LZY-82 and LZY-72, PQ Corporation's CP-304-37 and CP-316-26, UOP's Y-85, Y-84, LZ-10 and LZ-210.

The unit cell size and $SiO_2/Al_2O_3$ molar ratio for typical dealuminated Y-zeolites are noted in the following table:

| ZEOLITE TYPE | UNIT CELL SIZE, A | SiO2/Al2O3 MOLAR |
|---|---|---|
| LZY-82 | 24.53 | 7.8 |
| LZY-85 | 24.49 | 9.1 |
| LZY-10 | 24.32 | 23.7 |
| LZY-20 | 24.35 | 18.9 |
| LZY-84 | 24.51 | 8.4 |
| LZ-210 | 24.47 | 9.9 |
| LZY-72 | 24.52 | 8.1 |
| CP316-26 | 24.26 | 45.7 |

Said catalysts may be in the form of powders, pellets, granules, spheres, shapes and extrudates. The examples described herein demonstrate the advantages of using extrudates.

The reaction may be carried out in either a stirred slurry reactor or in a fixed bed continuous flow reactor. The catalyst concentration should be sufficient to provide the desired catalytic effect.

Dehydration to DIPE can generally be conducted at temperatures from 20° to 250° C.; the preferred range is 80° to 200° C. Good results are observed throughout this temperature range. However, it can be noted that the best conversion figures for MTBE, DIPE cogeneration are observed when the temperature is 120°–180° C. The total operating pressure may be from 0 to 5000 psig, or higher. The preferred pressure range is 100 to 1000 psi.

Typically, DIPE is generated continuously in up to ca. 13 wt % concentration or greater in the crude liquid product at total liquid hourly space velocities (LHSV) of up to 6 or higher and relatively mild conditions, where:

$$LHSV = \frac{\text{Volume Of Total Liquid Feed Run Through The Reactor Per Hour}}{\text{Volume of Catalyst In Reactor}}$$

Conversions of isopropanol (IPA) are estimated in the following examples using the equation:

$$\frac{(\text{Mole \% of IPA in Feed} - \text{Mole \% of IPA in Product})}{\text{Mole \% of IPA in Feed}} \times 100$$

The examples which follow illustrate the two-step synthesis of MTBE and DIPE from acetone also containing methanol plus t-butanol using β-zeolites, optionally modified with multiple metals, or dealuminized Y-zeolites.

Specifically accompanying examples illustrate:
1) The hydrogenation of crude acetone by-product stream from a PO/MTBE unit over a bulk metal, nickel-rich catalyst under moderate conditions (See Example 1).
2) The cogeneration of DIPE/MTBE from the hydrogenated acetone stream of Example 1 using a β-zeolite catalyst (See Example 2).
3) DIPE/MTBE generation from the hydrogenated acetone stream of Example 1 using:
   a. A dealuminized Y-zeolite, LZY-84 (Example 7, Table 7).
   b. A palladium-impregnated, fluorided β-zeolite (Example 3, Table 3).
   c. An iron, chromium, manganese-modified β-zeolite (Example 4, Table 4).
   d. A platinum-impregnated β-zeolite (Example 5, Table 5).
   e. A nickel, copper-treated β-zeolite (Example 6, Table 6).

EXAMPLE 1

This example illustrates the hydrogenation of a crude acetone stream.

A crude acetone mix from a PO/MTBE unit containing 62% acetone plus significant quantities of methanol and t-butanol and having the composition shown in Table 1 was passed, upflow, over a nickel, copper, chromium bulk metal catalyst containing about 72% nickel (Ni 2715, ⅛" Tablets from Engelhard Corp.) in the presence of hydrogen (90 l/hr) at LHSV of 0.5 at a series of temperatures (120°–160° C). Hydrogenation of said stream was achieved at 160° C. and a typical product composition for the liquid fraction is given in Table 1.

TABLE I

CRUDE ACETONE HYDROGENATION

| Ex. | Catalyst | Temp. (°C.) | LHSV | Sample | MeOH | Ac2O | IPA | tBA | tBF | ATBP |
|---|---|---|---|---|---|---|---|---|---|---|
| 1 | Ni 2715 ⅛" T | | | FS-1 | 13.9 | 61.7 | 0.1 | 16.7 | 0.1 | 3.3 |
| | | 160 | 0.5 | 1 | 15.8 | 0.8 | 48.3 | 30.8 | — | — |

[a] Designations: Methanol (MeOH), Acetone (Ac2O), Isopropanol (IPA), t-Butanol (tBA), t-Butyl Formate (tBF), Allyl t-Butyl Peroxide (ATBP).

EXAMPLE 2

This example illustrates the cogeneration of diisopropyl ether (DIPE) and methyl t-butyl ether (MTBE) from a hydrogenated acetone feedstock.

Synthesis was conducted in a tubular reactor (½" i.d., 12" long) constructed of 316 stainless steel, operated upflow, and mounted in a furnace, controllable to ±1.0° C., and fitted with pumps allowing flow control to <1 cc/hr. The reactor was also fitted with a pressure regulating device and equipment for monitoring temperature, pressure and flow rate.

The reactor was charged at the beginning of the experiment with 50 cc of β-zeolite (80% beta, 20% alumina binder, in 1/16" diameter extruded form, C861β from PQ Corp.). A glass wool screen was placed at the top and bottom of the reactor to ensure the catalyst would remain in the middle portion.

The catalyst bed was treated with the crude hydrogenated acetone feedstock of Example 1, while the reactor was held at a series of temperatures (120°–180° C.). Total unit pressure was maintained at 750 psi. Samples of crude product effluent were collected periodically on stream, in 316 ss bombs, and analyzed by glc and gc-ms. Typical analyses data are summarized in Table 2.

At 180° C., the isopropanol conversion level is 67% (Sample 6).

At 120° C., the major product is methyl t-butyl ether (MTBE).

At 180° C., the major products are diisopropyl ether (DIPE), methyl isopropyl ether (MIPE), plus some isopropyl t-butyl ether (IPTBE). Another co-product is diisobutylene ($C_8H_{16}$).

% Cr=0.19
% Mn=0.08
Acidity=0.35 meg/g

EXAMPLES 3-7

These examples illustrate the cogeneration of DIPE and MTBE using a series of metal-modified beta and dealuminated Y-zeolite catalysts.

Following the procedures and using the equipment of Example 2, a series of metal-modified beta and dealuminated Y-zeolite catalysts were used to cogenerate DIPE and MTBE from the hydrogenated acetone stream of Example 1.

Cogeneration of DIPE/MTBE was demonstrated using:

a) A palladium-impregnated, fluorided β-zeolite (Table 3).
b) An iron, chromium, manganese modified β-zeolite (Table 4).
c) A platinum-impregnated β-zeolite (Table 5).
d) A nickel, copper treated β-zeolite (Table 6).
e) A dealuminized Y-zeolite (Table 7).

EXAMPLE A

The example illustrates the preparation of a multimetal-modified β-zeolite. To 102 g of β-zeolite (Valfor C861β, 80% β-zeolite, 20% alumina) in 1/16" diameter extruded form was added a solution of ferric chloride hydrate (1.04 g), chromium(II) nitrate, hydrate (1.64 g) and manganese(II) nitrate hydrate (1.10 g) in 92 cc of distilled water. Impregnation of the β-zeolite was allowed to occur over 1-2 hours, then the solids were filtered off, dried at 120° C. overnight, and calcined at 315° C. for 2 hours, followed by 540° C. for another 2 hours.

The recovered green solid extrudates showed the presence of:

% Fe=0.27

TABLE 2

DIISOPROPYL ETHER SYNTHESIS

| Ex. | Catalyst | Temp. (°C.) | Sample | METHOD 27[a] | | | | | | | | | | | METHOD 26 | |
|---|---|---|---|---|---|---|---|---|---|---|---|---|---|---|---|---|
| | | | | DME | $C_4H_8$ | MeOH | MIPE | $Ac_2O$ | IPA | tBA | MTBE | IPTBE | IBA | $C_8H_{16}$ | $H_2O$ | DIPE |
| 2 | C861β | | Ex. 1 | | | 15.8 | | 0.8 | 48.3 | 30.8 | 0.1 | | 3.1 | | 5.7 | |
| | | 120 | 1 | 0.2 | 2.0 | 11.6 | 0.6 | 0.9 | 51.0 | 8.0 | 7.7 | 1.1 | 2.5 | 5.3 | 10.6 | 0.9 |
| | | | 2 | 0.2 | 2.1 | 12.4 | 0.6 | 1.3 | 46.4 | 9.3 | 8.1 | 1.3 | 2.6 | 5.7 | 10.5 | 0.9 |
| | | 140 | 1 | 1.6 | 2.2 | 12.8 | 1.7 | 2.7 | 41.7 | 5.2 | 4.5 | 0.9 | 2.6 | 7.9 | 13.6 | 2.6 |
| | | | 2 | 1.5 | 2.1 | 12.9 | 1.8 | 1.8 | 42.0 | 5.1 | 4.6 | 0.9 | 2.6 | 8.1 | 12.1 | 3.0 |
| | | 160 | 4 | 1.9 | 0.8 | 11.2 | 6.3 | 2.3 | 30.6 | 2.3 | 1.2 | 0.2 | 2.2 | 9.2 | b | b |
| | | | 5 | 2.8 | 1.0 | 10.9 | 6.6 | 2.3 | 29.3 | 1.8 | 1.2 | 0.2 | 2.1 | 9.1 | 16.5 | 9.1[c] |
| | | 180 | 5A | b | b | b | b | b | b | b | b | b | b | b | b | 13.9 |
| | | | 6 | 4.0 | 0.6 | 4.4 | 12.8 | 2.2 | 15.8 | 0.8 | 0.3 | 0.4 | 1.3 | 10.3 | 8.0 | 13.9 |

[a]Analysis on water-free basis
[b]Analyses not available

TABLE 3

DIISOPROPYL ETHER

| Ex. | Catalyst | Temp. (°C.) | Sample | METHOD 27 | | | | | | | | | | | METHOD 26 | |
|---|---|---|---|---|---|---|---|---|---|---|---|---|---|---|---|---|
| | | | | DME | $C_4H_8$ | MeOH | MIPE | $Ac_2O$ | IPA | tBA | MTBE | IPTBE | IBA | $C_8H_{16}$ | $H_2O$ | DIPE |
| 3 | 052-92-6887-021[a] | | Ex. 1 | | | 15.8 | | 0.6 | 48.4 | 30.9 | | | 3.1 | | 5.8 | |
| | | 120 | 1 | 0.1 | 6.6 | 11.9 | 0.3 | 0.8 | 46.7 | 10.5 | 9.9 | 2.3 | 2.4 | 3.6 | 10.3 | 1.6 |
| | | | 2 | 0.2 | 6.7 | 12.0 | 0.3 | 0.8 | 46.3 | 10.1 | 9.7 | 2.2 | 2.5 | 3.8 | 10.5 | 1.6 |
| | | 140 | 3 | 0.5 | 5.3 | 12.8 | 1.8 | 1.0 | 42.2 | 5.9 | 4.9 | 1.0 | 2.5 | 6.5 | 12.2 | 2.8 |
| | | | 4 | 0.6 | 5.3 | 12.7 | 1.9 | 1.1 | 42.0 | 5.7 | 5.0 | 1.0 | 2.4 | 6.6 | 12.0 | 3.1 |
| | | 160 | 5 | 1.1 | 3.0 | 10.9 | 6.7 | 1.4 | 31.0 | 1.5 | — | 0.3 | 2.0 | 8.0 | 15.9 | 8.7 |
| | | | 6 | 1.2 | 3.4 | 10.9 | 6.6 | 1.4 | 30.5 | 1.5 | | 0.3 | 2.0 | 8.0 | 16.2 | 8.3 |
| | | 180 | 7 | 1.8 | 1.7 | 5.5 | 13.2 | 1.6 | 18.4 | 0.6 | — | 0.2 | 1.2 | 9.6 | 8.4 | 12.7 |
| | | | 8 | 1.8 | 1.6 | 5.2 | 13.7 | 1.6 | 17.5 | 0.4 | | 0.1 | 1.1 | 9.7 | 8.8 | 12.3 |

[a]1% F(Calcined 540° C./2 hr), 0.3% Pd on 50% β-zeolite/alumina, reduced at 200° C., 1/16" E

TABLE 4

DIISOPROPYL ETHER

| Ex. | Catalyst | Temp. (°C.) | Sample | METHOD 27 | | | | | | | | | | | METHOD 26 | |
|---|---|---|---|---|---|---|---|---|---|---|---|---|---|---|---|---|
| | | | | DME | $C_4H_8$ | MeOH | MIPE | $Ac_2O$ | IPA | tBA | MTBE | IPTBE | IBA | $C_8H_{16}$ | $H_2O$ | DIPE |
| 4 | 052-92-6887-022[a] | | Ex. 1 | | | 15.2 | | | 50.2 | 29.8 | 0.1 | | 2.7 | | 5.7 | |
| | | 120 | 1 | 0.1 | 6.5 | 12.2 | 0.3 | 0.8 | 46.3 | 13.2 | 11.3 | 2.6 | 2.3 | 0.3 | 10.1 | 0.2 |
| | | | 2 | 0.1 | 7.0 | 12.2 | 0.2 | 0.7 | 46.3 | 12.9 | 11.4 | 2.7 | 2.3 | 0.3 | 10.1 | 0.2 |
| | | 140 | 3 | 0.2 | 7.8 | 12.8 | 0.4 | 2.2 | 45.0 | 9.8 | 8.5 | 2.0 | 2.3 | 1.2 | 11.1 | 0.6 |
| | | | 4 | 0.2 | 7.7 | 13.2 | 0.5 | 0.8 | 45.5 | 9.6 | 8.6 | 1.9 | 2.4 | 1.3 | 10.6 | 0.7 |
| | | 160 | 5 | 0.4 | 7.8 | 13.4 | 1.8 | 1.8 | 40.9 | 6.3 | 5.0 | 1.1 | 2.3 | 2.3 | 12.1 | 2.5 |
| | | | 6 | 0.4 | 7.6 | 13.2 | 1.7 | 4.2 | 39.9 | 6.1 | 4.9 | 1.1 | 2.2 | 2.2 | 11.7 | 2.4 |
| | | 180 | 7 | 1.2 | 3.3 | 12.9 | 4.5 | 1.6 | 36.0 | 4.8 | 2.7 | — | 0.1 | 7.9 | 14.9 | 5.5 |

TABLE 4-continued

DIISOPROPYL ETHER

| Ex. | Catalyst | Temp. (°C.) | Sample | METHOD 27 ||||||||||| METHOD 26 ||
|---|---|---|---|---|---|---|---|---|---|---|---|---|---|---|---|---|
| | | | | DME | $C_4H_8$ | MeOH | MIPE | $Ac_2O$ | IPA | tBA | MTBE | IPTBE | IBA | $C_8H_{16}$ | $H_2O$ | DIPE |
| | | | 8 | 1.3 | 3.5 | 12.8 | 4.6 | 1.6 | 35.5 | 4.5 | 2.6 | | 0.1 | 8.0 | 15.1 | 5.5 |

[a] 1% Fe, 1% Cr, 1% Mn or 60% β-zeolite/alumina, reduced at 350° C., 1/16" E

TABLE 5

DIISOPROPYL ETHER

| Ex. | Catalyst | Temp. (°C.) | Sample | METHOD 27 ||||||||||| METHOD 26 ||
|---|---|---|---|---|---|---|---|---|---|---|---|---|---|---|---|---|
| | | | | DME | $C_4H_8$ | MeOH | MIPE | $Ac_2O$ | IPA | tBA | MTBE | IPTBE | IBA | $C_8H_{16}$ | $H_2O$ | DIPE |
| 5 | 052-93-6895-026[a] | | Ex. 1 | | | 14.0 | | 0.7 | 52.4 | 28.8 | | | 2.8 | | 5.8 | |
| | | 120 | 1 | 0.4 | 2.8 | 13.0 | 0.5 | 1.2 | 46.4 | 10.8 | 9.0 | 1.1 | 2.0 | 4.3 | 9.3 | 0.8 |
| | | | 2 | 0.4 | 2.5 | 12.2 | 0.5 | 0.7 | 50.9 | 9.7 | 8.5 | 1.0 | 1.9 | 4.0 | 9.7 | 0.8 |
| | | 140 | 3 | 1.2 | 2.2 | 13.5 | 2.1 | 1.6 | 41.7 | 5.9 | 4.6 | 1.0 | 2.5 | 6.2 | 11.6 | 4.0 |
| | | | 4 | 1.2 | 2.3 | 13.5 | 2.2 | 1.5 | 41.2 | 5.9 | 4.6 | 1.0 | 2.4 | 6.2 | 12.3 | 3.7 |
| | | 160 | 5 | 1.3 | 0.8 | 13.2 | 6.2 | 2.0 | 31.2 | 3.8 | 1.4 | 0.3 | 2.1 | 7.4 | 16.6 | 8.5 |
| | | | 6 | 2.1 | 1.3 | 11.7 | 6.6 | 2.0 | 30.5 | 3.2 | 1.4 | 0.3 | 2.0 | 7.5 | 15.6 | 9.1 |
| | | 180 | 7 | 1.7 | 0.9 | 5.2 | 13.2 | 2.3 | 18.3 | 1.3 | 0.5 | 0.1 | 1.3 | 9.4 | 9.3 | 12.2 |
| | | | 8 | 1.7 | 0.9 | 5.2 | 12.8 | 2.3 | 17.9 | 1.2 | 0.4 | 0.1 | 1.3 | 9.4 | 9.5 | 12.3 |

[a] 0.3% Pt on 50% β-zeolite/alumina, reduced at 400° C., 1/16" E

TABLE 6

DIISOPROPYL ETHER

| Ex. | Catalyst | Temp. (°C.) | Sample | METHOD 27 ||||||||||| METHOD 26 ||
|---|---|---|---|---|---|---|---|---|---|---|---|---|---|---|---|---|
| | | | | DME | $C_4H_8$ | MeOH | MIPE | $Ac_2O$ | IPA | tBA | MTBE | IPTBE | IBA | $C_8H_{16}$ | $H_2O$ | DIPE |
| 6 | 052-93-6895-032[a] | | Ex. 1 | | | 15.4 | | 0.8 | 48.2 | 31.2 | | | 3.1 | | 5.8 | |
| | | 120 | 1 | 0.3 | 2.8 | 11.9 | 0.3 | 1.1 | 48.0 | 11.2 | 9.6 | 2.2 | 2.6 | 4.2 | 8.8 | 0.5 |
| | | | 2 | 0.3 | 2.9 | 12.0 | 0.3 | 1.1 | 47.9 | 10.3 | 9.9 | 2.3 | 2.6 | 4.5 | 9.7 | 0.4 |
| | | 140 | 3 | 1.0 | 2.4 | 12.9 | 1.4 | 1.4 | 43.5 | 5.8 | 4.9 | 1.0 | 2.5 | 8.0 | 11.5 | 2.4 |
| | | | 4 | 1.1 | 2.4 | 13.0 | 1.6 | 1.5 | 42.7 | 5.3 | 4.7 | 1.0 | 2.6 | 7.9 | 11.8 | 2.9 |
| | | 160 | 5 | 2.2 | 1.1 | 10.9 | 6.7 | 2.0 | 30.0 | 1.9 | 1.2 | 0.3 | 2.1 | 8.9 | 16.4 | 8.7 |
| | | | 6 | 2.1 | 1.1 | 10.9 | 6.4 | 2.0 | 29.9 | 1.9 | 1.1 | 0.2 | 2.0 | 9.0 | 15.7 | 9.8 |
| | | 180 | 7 | 3.2 | 0.6 | 4.4 | 13.6 | 2.7 | 15.7 | 0.8 | 0.3 | 0.3 | 0.2 | 9.8 | 7.5 | 13.8 |
| | | | 8 | 3.3 | 0.7 | 4.5 | 13.4 | 2.2 | 15.1 | 1.2 | 0.4 | 0.4 | 0.2 | 10.0 | 7.4 | 13.8 |

[a] 1% Ni, 1% Cu on 80% β-zeolite/alumina, reduced at 350° C., 1/16" E

TABLE 7

DIISOPROPYL ETHER SYNTHESIS

| Ex. | Catalyst | Temp. (°C.) | Sample | METHOD 27 ||||||||||| METHOD 26 ||
|---|---|---|---|---|---|---|---|---|---|---|---|---|---|---|---|---|
| | | | | DME | $C_4H_8$ | MeOH | MIPE | $Ac_2O$ | IPA | tBA | MTBE | IPTBE | IBA | $C_8H_{16}$ | $H_2O$ | DIPE |
| 7 | LZY-84 | | Ex. 1 | | | 16.0 | | 0.8 | 48.2 | 30.7 | 0.1 | | 3.0 | | 5.7 | |
| | | 120 | 1 | — | 4.7 | 12.0 | 0.1 | 0.9 | 48.7 | 13.6 | 11.8 | 3.1 | 2.6 | 0.1 | 9.9 | 0.1 |
| | | | 2 | | 4.7 | 11.9 | 0.1 | 1.7 | 48.5 | 13.7 | 11.6 | 3.1 | 2.6 | 0.1 | 9.9 | — |
| | | 140 | 3 | 0.1 | 7.0 | 12.1 | 0.6 | 1.0 | 48.2 | 11.7 | 11.0 | 2.7 | 2.6 | 0.5 | 10.5 | 0.1 |
| | | | 4 | 0.1 | 7.1 | 12.1 | 0.2 | 1.8 | 47.9 | 11.2 | 11.1 | 2.7 | 2.5 | 0.5 | 9.8 | 0.2 |
| | | 160 | 5 | 0.4 | 8.7 | 12.9 | 0.9 | 1.2 | 45.9 | 9.2 | 8.5 | 2.0 | 2.5 | 2.4 | 10.6 | 1.0 |
| | | | 6 | 0.4 | 8.4 | 12.7 | 0.9 | 1.2 | 46.5 | 9.1 | 8.4 | 2.0 | 2.6 | 2.4 | 10.2 | 1.0 |
| | | 180 | 7 | 1.3 | 7.7 | 12.0 | 4.0 | 1.6 | 37.5 | 6.7 | 4.5 | 1.1 | 2.6 | 6.4 | 12.8 | 3.8 |
| | | | 8 | 1.2 | 7.7 | 12.0 | 3.9 | 1.6 | 37.5 | 6.7 | 4.6 | 1.1 | 2.5 | 6.4 | 12.9 | 3.8 |

What is claimed is:

1. A two-step process for the cogeneration of diisopropyl ether and methyl tertiary butyl ether (MTBE) from a crude by-product acetone stream from a process to produce MTBE or other oxygenates, said stream containing greater than 5% of both methanol and t-butanol, which comprises:

(a) Hydrogenating said crude acetone over a nickel-rich catalyst consisting essentially of 60–85 mol % nickel, 1–30 mol % copper and 0.1–6 mol % chromium at a temperature in the range 120° C.–180° C., and (b) subjecting said isopropanol-rich intermediate to dehydration conditions, including a temperature in the rang of 80° C. to 200° C., in the presence of a strong acid zeolite catalyst selected from the group consisting of β-zeolite, optionally modified with one or more metals selected from the group consisting of Group IB, VIB, VIIB and VIII of the Periodic Table, and dealuminized Y-zeolite.

2. The process of claim 1 wherein the β-zeolite has a silica:alumina molar ratio of at least 10:1.

3. The process of claim 1 wherein the β-zeolite has a silica:alumina molar ratio in the range of 10:1 to 50:1.

4. The process of claim 1 wherein the β-zeolite has a surface area, after calcination, at least 100 m²/g.

5. The process of claim 1 wherein the β-zeolite is characterized by the following X-ray diffraction, pattern:
11.40±0.2
7.40±0.2
6.70±0.2
4.25±0.1
3.97±0.1
3.00±0.1
2.20±0.1

6. The process of claim 1 wherein the β-zeolite is modified with one or more metals from Groups IB, VIB, VIIB or VIII of the Periodic Table.

7. The process of claim 6 wherein the β-zeolite is modified with one or more metals selected from the group consisting of iron, chromium, manganese, copper, nickel, palladium and platinum.

8. The process of claim 7 wherein the β-zeolite is modified with one or more metals selected from the group consisting of iron, chromium and manganese.

9. The process of claim 1 wherein the concentrations of metals modifying said zeolite may vary from 0.01% to 10.0% for each metal.

10. The process of claim 7 wherein said β-zeolite is treated with a fluoride-containing compound.

11. The process of claim 1 wherein the β-zeolite catalyst is formed in the presence of a binder selected from a Group III oxide or a Group IV oxide.

12. The process of claim 11 wherein the Group III oxide binder is alumina.

13. The process of claim 11 wherein the alumina comprises 10% to 90% of the formed catalyst.

14. The process of claim 1 wherein the second stage catalyst is dealuminated Y-zeolite dealuminated in a manner selected from the group consisting of:
 a) ammonium exchanging the Y-zeolite followed by calcinating;
 b) by treating with ethylenediaminetetraacetic acid.
 c) treating the Y-zeolite with a fluorine-containing compound selected from the group consisting of silicon tetrafluoride and ammonium fluorosilicate; or
 d) treating the Y-zeolite with steam alone or followed by acid treatment.

15. The process of claim 14 wherein the dealuminized Y-zeolite has a silica-to-alumina molar ratio of greater than 3.

16. The process of claim 15 wherein the dealuminized Y-zeolite has a silica-to-alumina molar ratio in the range 5 to 25 and a unit cell size in the range 24.32 to 24.53.

17. The process of claim 1 wherein the crude by-product acetone stream contains 20% to 80% acetone.

18. The process of claim 1 wherein the methanol and t-butanol contents of the acetone by-product stream are in the range 10% to 40%.

19. A two-step process for the cogeneration of diisopropyl ether and methyl tertiary butyl ether from a crude acetone stream from a process to produce MTBE or other oxygenates, said stream containing greater than 5% of both methanol and t-butanol, which comprises;
 (a) Hydrogenating said crude acetone over a nickel catalyst consisting essentially of 60–85% mol % nickel, 1–30 mol % copper and 0.1–6 mol % chromium at a temperature in the range 120° C.–180° C. to give an isopropanol-rich effluent; and
 (b) subjecting said isopropanol-rich intermediate to dehydration conditions, including a temperature in the range 80° C.–200° C. in the presence of a strong acid zeolite catalyst selected from the group consisting of β-zeolite, optionally modified with one or more metals selected from the group consisting Group IB, VIB, VIIB and VIII of the Periodic Table, and a dealuminized Y-zeolite.

* * * * *

UNITED STATES PATENT AND TRADEMARK OFFICE
CERTIFICATE OF CORRECTION

PATENT NO. : 5,430,198

DATED : July 4, 1995

INVENTOR(S) : John Frederick Knifton and Pei-Shing Eugene Dai

It is certified that error appears in the above-identified patent and that said Letters Patent is hereby corrected as shown below:

Col. 1, line 1, delete "EHTER" and insert therefor -- ETHER --.

Cover Sheet, in the title, delete "EHTER" AND Insert therefor -- ETHER --.

Signed and Sealed this

Third Day of October, 1995

Attest:

BRUCE LEHMAN

Attesting Officer

Commissioner of Patents and Trademarks